United States Patent
Beoni

(10) Patent No.: US 9,387,070 B2
(45) Date of Patent: Jul. 12, 2016

(54) PROSTHETIC ELEMENT FOR CONNECTING THE STAPES FOOTPLATE TO A MIDDLE EAR OSSICULAR PROSTHESIS

(71) Applicant: Franco Beoni, Piacenza (IT)

(72) Inventor: Franco Beoni, Piacenza (IT)

(*) Notice: Subject to any disclaimer, the term of this patent is extended or adjusted under 35 U.S.C. 154(b) by 12 days.

(21) Appl. No.: 14/277,220

(22) Filed: May 14, 2014

(65) Prior Publication Data

US 2014/0343674 A1 Nov. 20, 2014

(30) Foreign Application Priority Data

May 17, 2013 (EP) ..................................... 13168303

(51) Int. Cl.
*A61F 2/18* (2006.01)

(52) U.S. Cl.
CPC ............. *A61F 2/18* (2013.01); *A61F 2002/183* (2013.01); *A61F 2220/0016* (2013.01); *A61F 2220/0025* (2013.01); *A61F 2220/0033* (2013.01); *A61F 2220/0091* (2013.01); *A61F 2230/0006* (2013.01); *A61F 2230/0019* (2013.01); *A61F 2230/0069* (2013.01); *A61F 2250/001* (2013.01); *A61F 2250/006* (2013.01); *A61F 2250/0026* (2013.01)

(58) Field of Classification Search
CPC ................ A61F 2/18; A61F 2002/183; A61F 2002/30894; A61F 2002/30896; A61F 2002/30878; A61F 2002/30891; A61F 2002/30892; A61F 11/004; A61F 11/008; A61B 17/8695; A61B 17/8028; A61B 17/6839; A61L 2430/14; A61N 1/0541; A61N 1/36032

See application file for complete search history.

(56) References Cited

U.S. PATENT DOCUMENTS

| | | | | |
|---|---|---|---|---|
| 4,510,627 A | * | 4/1985 | Treace | A61F 2/18 623/10 |
| 4,624,672 A | * | 11/1986 | Lenkauskas | A61F 2/18 128/864 |

(Continued)

FOREIGN PATENT DOCUMENTS

| | | | |
|---|---|---|---|
| DE | 3901796 A1 | * 7/1990 | .............. A61F 2/18 |
| DE | 202004012134 U1 | 12/2004 | |

(Continued)

OTHER PUBLICATIONS

European Search Report and Written Opinion dated Jul. 29, 2013 for European patent application No. 13168303.9.

*Primary Examiner* — Andrew Iwamaye
(74) *Attorney, Agent, or Firm* — Vorys, Sater, Seymour and Pease LLP

(57) ABSTRACT

A prosthetic element enables the stapes footplate to be connected to the foot of a middle ear ossicular prosthesis. The prosthetic connection element is of biocompatible material and forms part of the foot or is connected or connectable to this latter, and includes a body provided with a flat surface intended to rest on the footplate and having an area sufficient to prevent reabsorption of the footplate osseous tissue as a result of the pressure which the ossicular prosthesis exerts on the footplate. The prosthetic element includes at least two pointed projections projecting from the flat surface and to penetrate the footplate.

26 Claims, 5 Drawing Sheets

(56) References Cited

U.S. PATENT DOCUMENTS

| | | | | |
|---|---|---|---|---|
| 4,641,651 | A | * | 2/1987 | Card .................. A61B 17/32 606/184 |
| 4,740,209 | A | * | 4/1988 | Gersdorff ............... A61F 2/18 623/10 |
| 5,104,401 | A | | 4/1992 | Kurz |
| 5,236,455 | A | * | 8/1993 | Wilk et al. ..................... 623/10 |
| 2002/0045939 | A1 | * | 4/2002 | Kurz ............................ 623/10 |
| 2010/0100180 | A1 | | 4/2010 | Beoni |
| 2011/0046731 | A1 | * | 2/2011 | Wiens .................. A61F 2/18 623/10 |
| 2011/0066240 | A1 | | 3/2011 | Beoni |
| 2011/0178364 | A1 | * | 7/2011 | Ball et al. ...................... 600/25 |
| 2013/0018217 | A1 | * | 1/2013 | Santek et al. ................... 600/25 |
| 2013/0053957 | A1 | * | 2/2013 | Scheurer ................ A61F 2/18 623/10 |

FOREIGN PATENT DOCUMENTS

| | | | | |
|---|---|---|---|---|
| DE | 102009006047 | B3 | * 3/2010 | ............... A61F 2/18 |
| EP | 0379740 | A1 | 8/1990 | |
| EP | 0563767 | A1 | 10/1993 | |
| EP | 2135584 | B1 | 1/2011 | |
| EP | 2238945 | B1 | 9/2011 | |
| ZA | WO 2013138818 | A1 | * 9/2013 | ............... A61F 2/18 |

* cited by examiner

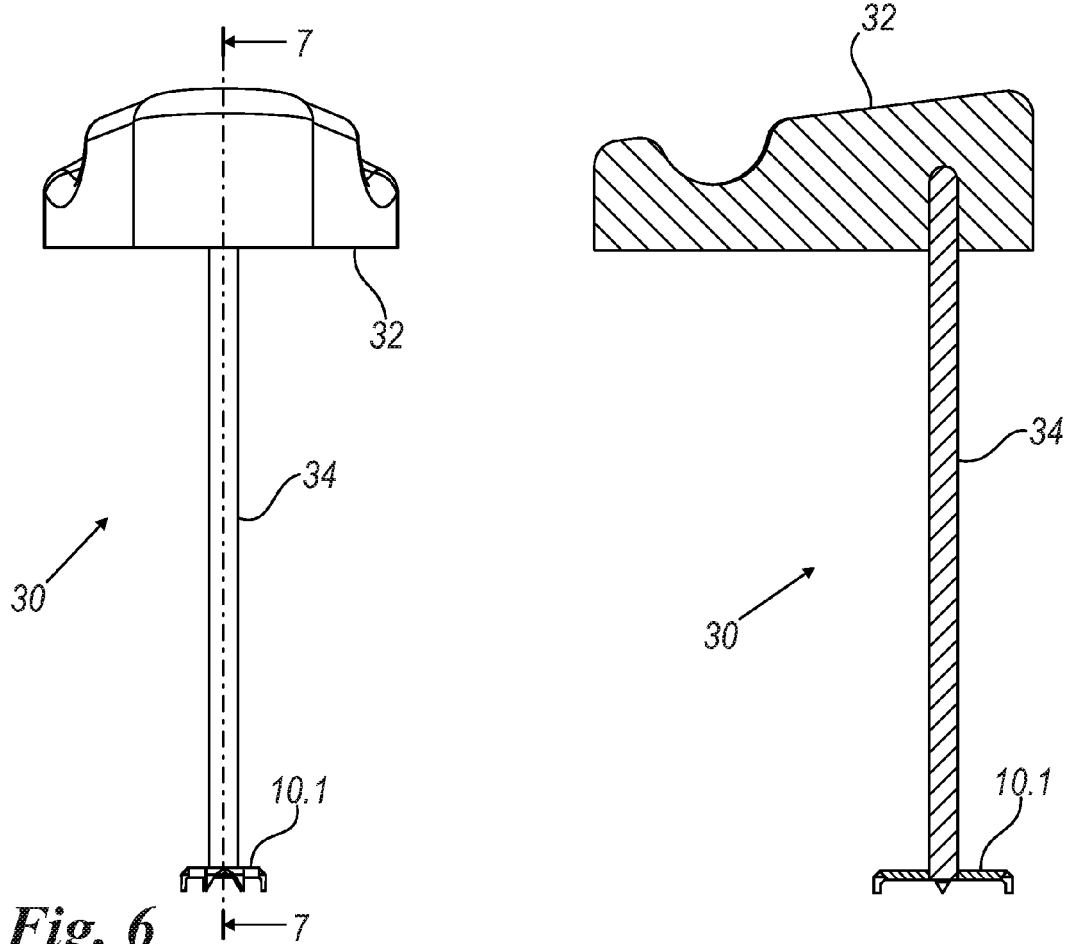
Fig. 6  Fig. 7
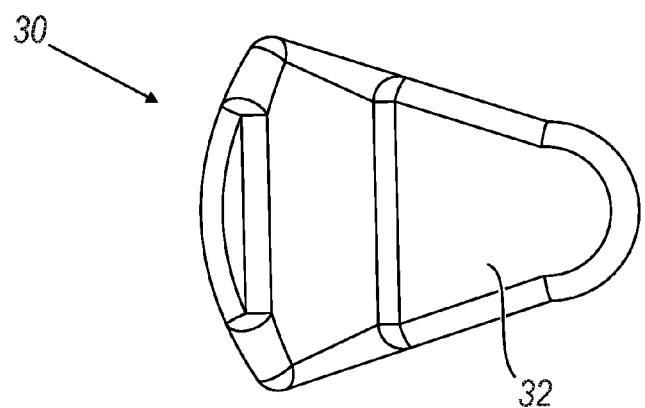
Fig. 8

PROSTHETIC ELEMENT FOR CONNECTING THE STAPES FOOTPLATE TO A MIDDLE EAR OSSICULAR PROSTHESIS

CROSS-REFERENCE TO RELATED APPLICATIONS

This claims the priority benefit of European Patent Application no. 13168303.9 filed May 17, 2013, incorporated herein by reference in its entirety.

The present invention concerns tympanoplasty, i.e. the reconstruction of the tympanum and of the middle ear ossicular chain after destruction by chronic otitis, and in particular ossiculoplasty, i.e. the partial or total reconstruction of the ossicular chain, and more specifically relates to a prosthetic element which enables the stapes footplate to be connected to a prosthesis intended to replace the ossicular chain.

Prostheses for ossiculoplasty have been in use for many decades in a large variety of forms and constructed of various materials. In particular, those prostheses for reconstructing the entire ossicular chain are known as "total", having one end, known as the flange, to be connected to the neotympanum or to the ossicle remnant known as the hammer, whereas the opposite end of the prosthesis, known as the foot, is intended to rest on the stapes footplate (i.e. that part of the stapes which remains in situ, its claws having been destroyed). The foot consists of the free end of a so-called shank, the other end of which is fixed to said flange.

Although the flange and shank of these ossicular prostheses have been subjected to many improvements over the years, up to a short time ago the relative foot had remained unvaried and consisted simply of the cylindrical end of the shank, intended to rest directly on the central zone of the footplate.

It should be noted that the auditory recovery achieved by ossiculoplasty takes place and is maintained with time only if, besides having a perfectly mobile footplate, the prosthesis foot rests in the central zone of the footplate and does not shift from this position with time. Unfortunately, this ideal situation is still not achieved in many cases. It can in fact happen that the overall prosthesis or just its foot becomes displaced or slips because of trauma or cicatrisation, such that contact between the foot of the ossicular prosthesis and the footplate central zone no longer exists. The result is loss of hearing.

Only recently has the attention of surgeons been focused on preventing occurrence of this problem.

The solutions adopted up to the present time comprise the use of a prosthetic element (known in the sector as a "shoe") which increases the surface of contact with the stapes footplate (the footplate is the only part of the original stapes which is present in all cases) and which is connected to relative end, or foot, of the shank of the ossicular prosthesis used.

In a known embodiment of this shoe, it has a substantially rectangular body with a flat face intended to rest on the footplate, whereas the opposite face of the body presents a cavity arranged to receive the foot of the ossicular prosthesis.

In another known embodiment, on the face-opposed to the flat face of the shoe body an ogival apophysis is present, received in a corresponding cavity provided in the relative foot of the ossicular prosthesis (the foot of the shank must hence be suitably shaped).

As stated, the use of these shoes enables the area of contact with the footplate surface to be increased, representing an improvement on the previous situation (in which the contact surface was limited to the relative end surface of the cylindrical shank). The mere increase of the surface of contact with the footplate achieved by these shoes is not always sufficient to prevent displacement of the ossicular prosthesis foot.

The object of the present invention is to provide a prosthetic element for connection between the footplate and foot of an ossicular prosthesis which solves the aforestated technical problem, such that the aforedescribed problem is no longer present.

This object is attained by the prosthetic connection element in accordance with claim 1.

Other features of this prosthetic element are defined in the dependent claims.

The invention will be more easily understood from the ensuing description of some embodiments thereof, given by way of example. In this description, reference will be made to the accompanying drawings, in which:

FIG. 6 is an elevation, again enlarged compared with its actual size, of a first known total ossicular prosthesis, of the type provided with a flange, in which the prosthetic connection element according to the present invention is already fixed directly to the foot of the prosthesis shank;

FIG. 7 is a section therethrough on the line 7-7 of FIG. 6;

FIG. 8 is a plan view thereof from above;

FIGS. 1-4 show an embodiment of the prosthetic connection element 10 according to the present invention, which in this case is constructed independently of the ossicular prosthesis to which it is applied only subsequently, and which enables the stapes footplate to be reliably connected (as will be seen) to the relative end, or foot, of the shank of said prosthesis.

Figure 1:
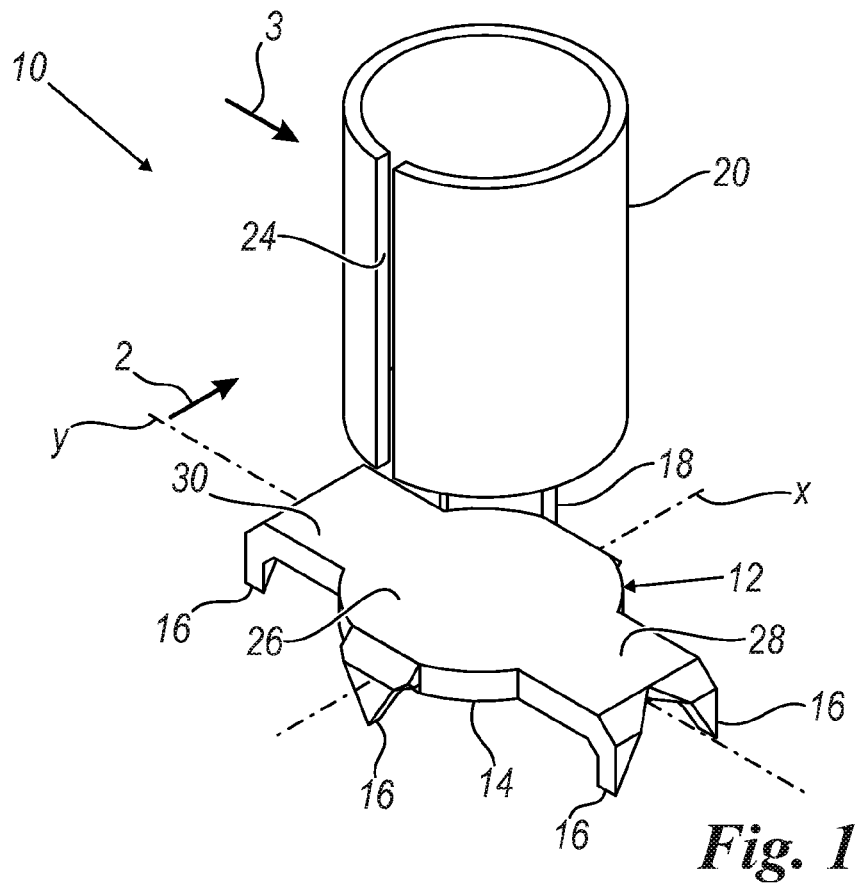
FIG. 1 is a perspective view, enlarged compared with its actual size, of a connection element according to the present invention, of the type connectable to the foot of a conventional ossicular prosthesis.
Figure 2:
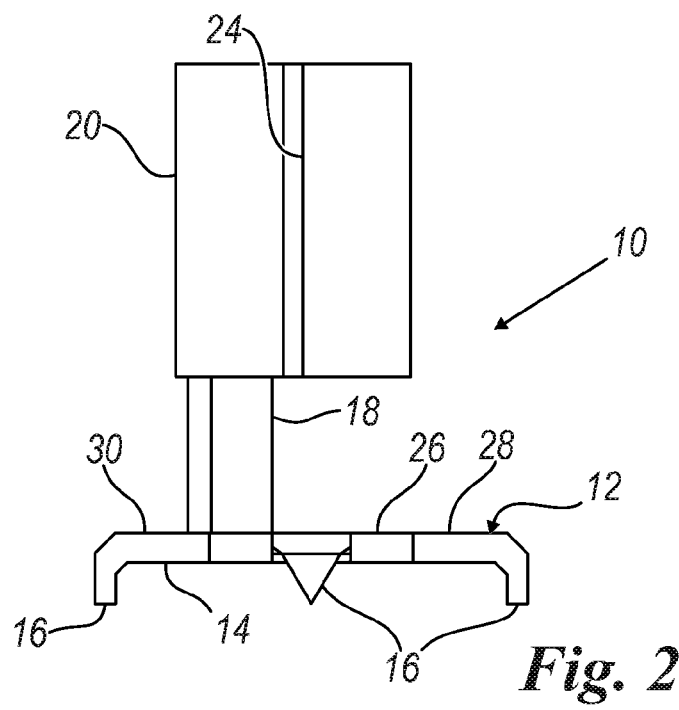
FIG. 2 is an elevation thereof in the direction of the arrow 2 of FIG. 1.
Figure 3:
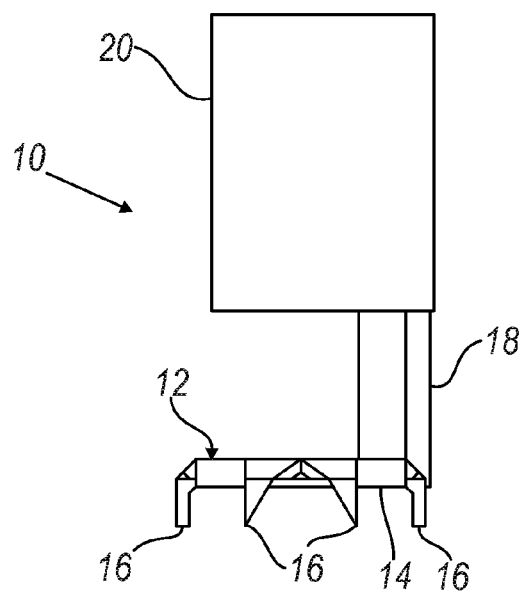
FIG. 3 is an elevation thereof in the direction of the arrow 3 of FIG. 1.
Figure 4:
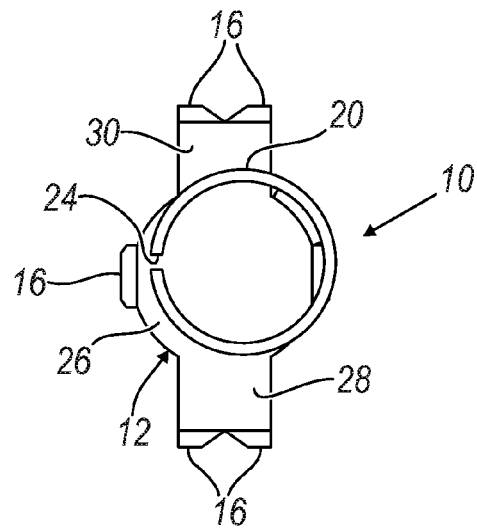
FIG. 4 is a plan view thereof from above.

As can be seen from FIGS. 1-4, the prosthetic connection element shown therein, indicated by 10, comprises a flat body 12 from the edge of the flat lower surface 14 of which there downwardly extend six pointed projections 16 distributed along said edge. In the specific illustrated case the lower surface 14 presents two mutually perpendicular axes of symmetry, namely an axis X in the direction of the minor dimension of the body 12 and an axis Y in the direction of the major dimension thereof. From these figures it can also be seen that the pointed projections 16 in this case are distributed symmetrically about both the axis X and the axis Y and that the flat body 12 consists (see FIGS. 1 and 4 in particular), of a substantially circular central part 26, from the two opposite sides of which there outwardly extend two substantially rectangular equal and symmetrical parts 28 and 30.

The shape of the flat body 12 and its two sizes have been designed to adapt to the shape of the footplate, which is substantially elliptical, and on which the body 12 must be centred without extending beyond the edges. In particular, the axis Y of the surface 14 is intended to coincide with the major axis of the footplate once the ossicular prosthesis has been positioned in situ.

A vertical arm 18 connects the flat body 12 to a longitudinally split cylindrical sleeve 20. The sleeve 20 essentially forms a connection means enabling the surgeon, by simply squeezing the sleeve 20 using suitable grips, to fix the prosthetic connection element 10 to the cylindrical foot, previously inserted into said sleeve, of a conventional ossicular prosthesis. From the aforegoing, it is apparent that the prosthetic element 10 can be used with any ossicular prosthesis, provided the sleeve 10 is able to receive the foot of the prosthesis and then be squeezed thereagainst, independently of the type of foot material.

It will be apparent to the expert of the art that other types of connection means (in particular different from a sleeve to be squeezed, for example a spherical hinge) can be used to make the connection between the prosthetic element according to the present invention and the prosthesis foot.

Returning to FIGS. 1-4, when the surgeon, using conventional surgical techniques, inserts into the patient's middle ear a conventional ossicular prosthesis (to which the prosthetic connection element 10 has already been applied in the aforedescribed manner, with the flat surface 14 centred on the elliptical footplate with the axis Y coinciding with the major axis of the footplate), the pointed projections 16 are the first to come into contact with the footplate surface. As is known to the expert of the art, when the ossicular prosthesis is located in position within the patient's middle ear, it presses lightly on the footplate. It is known from histology that if a sufficient pressure is applied within a limited zone of a bone, the phenomenon of osseous reabsorption (compressive osteolysis) is triggered within that zone. Consequently, when the prosthesis is in position, the pressure exerted by the pointed projections 16 on the footplate surface gradually causes reabsorption of the respective footplate osseous tissue, so that the pointed projections 16 gradually penetrate into the footplate, until contact exists between the footplate and the lower surface 14 of the flat body 12 of the prosthetic connection element 10. Obviously the extent of said lower surface 14 must be sufficient such that when it comes into contact with the footplate, the pressure exerted on this latter by said surface does not cause further reabsorption of the footplate osseous tissue. To prevent this, a surface of a fairly limited extent is in fact sufficient, seeing that the surface area by which the cylindrical foot (normally of diameter 0.6-0.8 mm) rests on the footplate of a conventional ossicular prosthesis is sufficient to prevent osseous reabsorption. When the pointed projections 16 have penetrated into the bone of the footplate, any slippage or displacement of the flat body 12 is evidently prevented, as is consequently that of the foot of the prosthesis shank, in any direction parallel to the footplate surface.

With regard to the specific case of FIGS. 1-4, although six pointed projections 16 are provided, it will be apparent that only two pointed projections disposed in opposing positions are sufficient to prevent any slippage.

Preferably the pointed projections 16 project from the surface 14 by less than the thickness of the footplate (which is normally greater than 0.25 mm), although a penetration of the pointed projections 16 slightly beyond the footplate thickness does not create particular problems.

Figure 5:
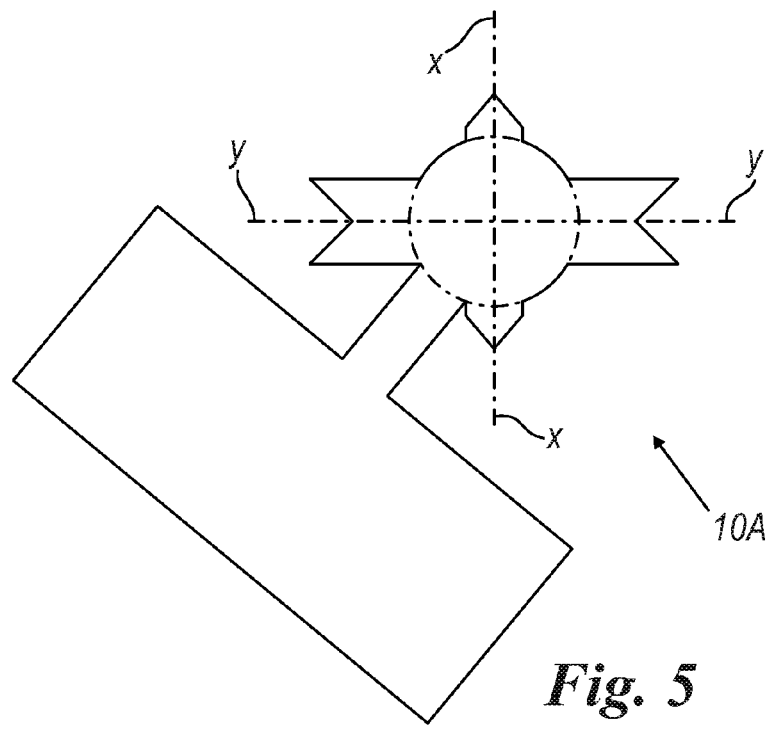
FIG. 5 is a plan view of the shaped sheet portion from which the connection element of the previous figures can be obtained by simple bending.

The prosthetic connection element 10 can be conveniently obtained by bending in an evident manner the shaped sheet portion 10A of FIG. 5, itself obtained from a sheet of biocompatible metal, for example titanium, of suitable thickness (for example 0.075 mm). Observing FIG. 5, it can be seen which of the various parts of the profiled sheet portion 10A give rise, after bending, to the respective parts of the prosthetic connection element 10. The same figure also shows the axes X and Y intended to become the mutually perpendicular axes of symmetry of said flat surface 14.

By way of example, the length of the flat body 12 of the connection element 10 can be 1.200 mm and its width 0.700 mm, while the sleeve 20 can have a height of 0.800 mm and an outer diameter of 0.600 mm. The diameter is in any event chosen such as to be able to receive the foot of the shank of the relative ossicular prosthesis. The longitudinal slit 24, originated by the manner in which the prosthetic element 10 is constructed starting from the sheet portion 10A, can facilitate the operation of squeezing the sleeve 20 about the foot of the ossicular prosthesis, such that it remains fixed to it.

The prosthetic connection element according to the present invention can however be preferably formed such that its body already forms part of the foot of the ossicular prosthesis on constructing this latter, and in particular form a single piece with this foot, or be already connected to this latter. This can be achieved for example by welding the prosthetic element 10, without however the sleeve 20 and connection 18 (which are no longer required), to the foot (for example by laser).

Examples of ossicular prostheses of which the foot is already provided with a prosthetic connection element according to the invention are visible in FIGS. 6-12. In particular, FIGS. 6-8 show a known ossicular prosthesis 30 with a bioceramic flange 32 and a rectilinear shank 34 of titanium, the lower end or foot of which forms one piece with a prosthetic connection element 10.1 according to the present invention. As can be seen, the prosthetic element 10.1 consists essentially of the body 12 of the prosthetic element 10.

It is however apparent that the prosthetic element 10 can also be used with the ossicular prosthesis 30. To achieve this is sufficient to connect this latter to its foot by simply squeezing the sleeve 20.

The body 12 can evidently have a shape different from that shown in the relative figures, while still falling within the scope of protection of the present invention, and/or the number and shape of the relative projections can also be different.

Figure 9:
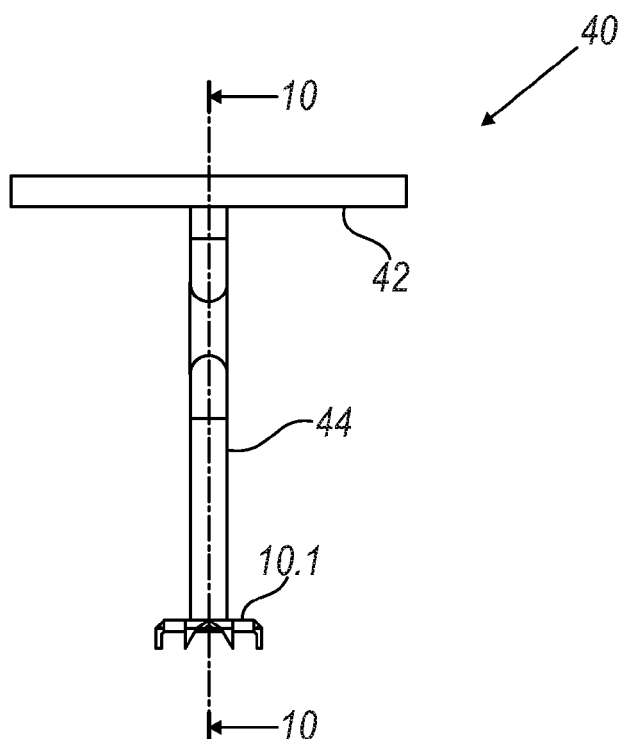
FIG. 9 is an elevation, again enlarged, of a second known total ossicular prosthesis, provided with a different type of flange, in which the prosthetic connection element according to the present invention is again already fixed directly to the foot of the prosthesis shank.
Figure 10:
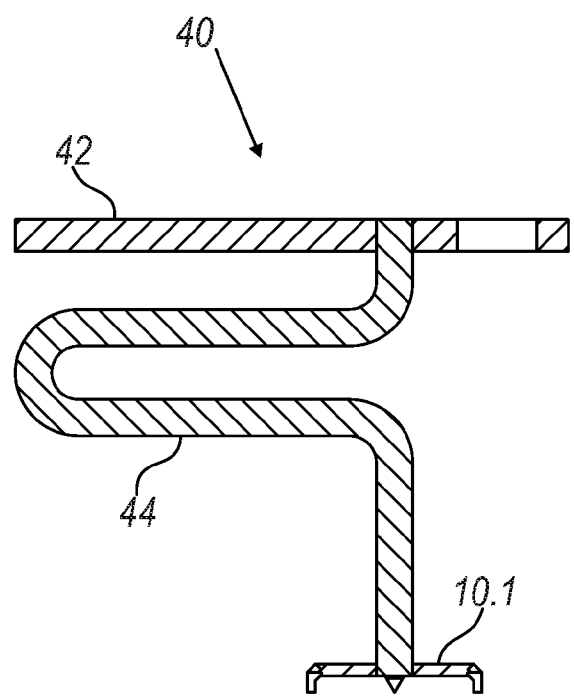
FIG. 10 is a section therethrough on the line 10-10 of FIG. 9.
Figure 11:
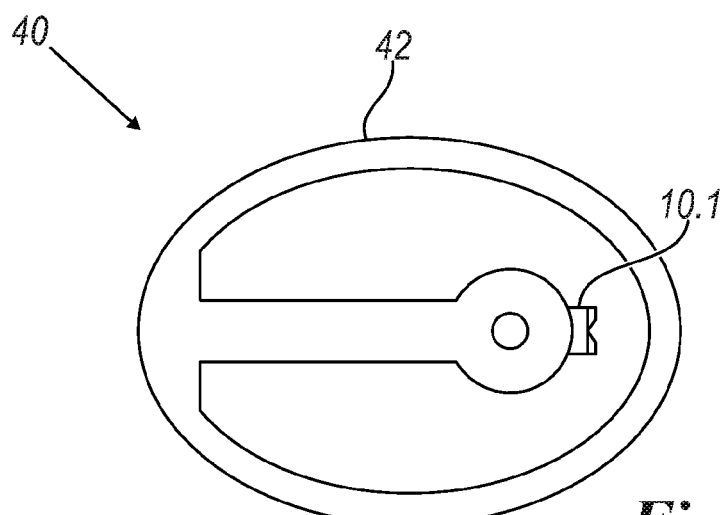
FIG. 11 is a plan view thereof from above.

Another example of a known ossicular prosthesis with which the prosthetic connection element according to the present invention can be used, and in particular the same prosthetic element 10.1 used with the ossicular prosthesis 30, is visible in FIGS. 9-11 (in which the prosthesis is indicated by 40 and is of the type with an oval annular flange 42 and a gooseneck shank 44, to obtain a lengthenable shank). Again in this case, the prosthetic element 10.1 can obviously be replaced by the prosthetic element 10 of FIGS. 1-4.

Figure 12:
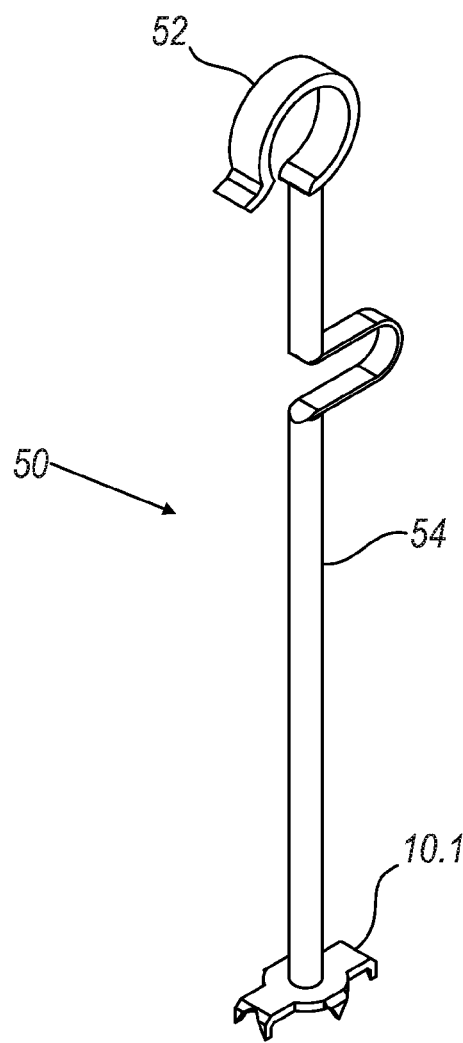
FIG. 12 is an enlarged perspective view of a third known ossicular prosthesis, of the type usable when the incus or the hammer are still present so that the flange is not provided, it being arranged to be coupled to the incus or to the hammer, with the prosthetic connection element of the present invention already fixed directly to the foot of the prosthesis shank.

FIG. 12 shows how the prosthetic connection element according to the present invention, and in particular the prosthetic element 10.1, can also be used with an ossicular prosthesis without a flange, and in particular of the type which can be hooked to the incus or to the hammer (provided these are still present), namely the prosthesis indicated by 50. For this purpose this prostheses is provided with a hook 52 and a gooseneck shank 54 (so that it can be lengthened). If required, the prosthetic connection element of FIGS. 1-4 can also be used with this prosthesis. It should be noted that the prosthesis

50 can obviously also form part of the middle ear prosthetic device of EP-B-2135584 or EP-B-2238945 the inventor of which is the same as of the present invention.

As already stated, the pointed projections 16 of the prosthetic connection elements 10 and 10.1 visible in the figures could have a shape different from that shown therein, and in particular a conical or triangular or square based pyramidal shape, or again be of needle or lamina shape, provided they are able to penetrate into the footplate by compressive osteolysis, all these embodiments being included in the wording "pointed projections".

It is important to note that the prosthetic connection element of the present invention enables another significant result to be achieved. From human anatomy the stapes, and more precisely its footplate, is known to be positioned in a substantially elliptical cavity, known as the oval window, which forms the passage element between the middle ear and the inner ear in which the acoustic nerve receptor, i.e. the cochlea, is located. The footplate, which is also elliptical, is centred within the oval window and joined to the edges of this latter by the annular ligament which surrounds it and which, being elastic, enables the footplate to vibrate.

From human physiology it is also known that the vibratory movements of the stapes are not of "piston" type (i.e. in the direction of the axis perpendicular to the plane of the oval window), but are vibratory rocking or pitching movements, i.e. the stapes footplate rocks in the direction of the major axis of the oval window, by rotating substantially about the minor axis of the footplate. This takes place because the incus ossicle transmits vibrations to the stapes capitulum, from which the two claws of the stapes extend. The other end of each of these two claws is fixed to corresponding points of the footplate lying on the major axis of this latter (which, as stated, is elliptical), each close to the respective ends of the footplate.

At this point it should be noted that of all the total ossicular prostheses (i.e. those which rest on the footplate) constructed up to the present time, none is able to impress the aforedescribed rocking movement on the footplate, as they do not form a structure adapted to reproduce the structure constituted by the stapes, not only for total prostheses with a cylindrical foot, but also if a shoe of the aforedescribed type is provided. The reason is that they do not form a single piece with the footplate.

It has been verified that by virtue of the connection element according to the present invention it is instead possible to obtain a rocking movement of the footplate in the required direction (that of the major axis of the oval window), hence reproducing the real anatomical and physiological situation of the footplate.

In conclusion it should be noted that the prosthetic connection element according to the present invention enables the aforesaid problem presented by known shoes to be completely obviated in a simple and practical manner, so that it provides a guarantee against the interruption of transmission of sound waves between the neotympanum and footplate due to slippage of the foot of the ossicular prosthesis. It also enables the sound wave to be transmitted to the inner ear by footplate rocking movements, precisely as takes place in human physiology, with evident optimal auditory recovery results.

The invention claimed is:

1. A prosthetic connection element for connecting a stapes footplate of a human patient to a middle ear ossicular prosthesis, the prosthetic connection element being of biocompatible material and forming part of a foot of said middle ear ossicular prosthesis or being connected or connectable to said foot, the prosthetic connection element comprising
   a flat body provided with
      a flat surface intended to rest on the stapes footplate, the flat body and flat surface sized to not extend beyond edges of the stapes footplate when the flat body rests on the stapes footplate, the flat surface having an area sufficient to prevent reabsorption of osseous tissue of the stapes footplate, and
   at least two pointed projections, the at least two pointed projections individually projecting from said flat body and away from said flat body and flat surface, each of said at least two pointed projections having
      (1) a first portion directly extending obliquely, outwardly, downwardly, and distally from edges of the flat body, and
      (2) a second portion extending distally from the first portion, the second portion comprising a tapered pointed distal end to penetrate the stapes footplate, the second portion extending substantially perpendicular to a plane on which the flat surface lies.

2. The prosthetic connection element as claimed in claim 1, wherein the flat body has an axis of symmetry, the at least two pointed projections being distributed symmetrically about said axis of symmetry.

3. A prosthetic connection element as claimed in claim 2, wherein the flat body has a second axis of symmetry perpendicular to the first axis of symmetry, the at least two pointed projections being distributed symmetrically about both the first and second axes of symmetry.

4. The prosthetic connection element as claimed in claim 2, wherein the flat surface extends continuously across the axis of symmetry.

5. The prosthetic connection element as claimed in claim 2, wherein, if the prosthetic connection element is not already connected to the foot of the middle ear ossicular prosthesis, a means is provided enabling the prosthetic connection element to be connected to the foot of the middle ear ossicular prosthesis.

6. The prosthetic connection element as claimed in claim 2, wherein if the prosthetic connection element is not already connected to the foot of the middle ear ossicular prosthesis a sleeve is fixed to the flat body, the sleeve being adapted to receive the foot of the middle ear ossicular prosthesis to ensure a connection with said foot by squeezing the sleeve.

7. The prosthetic connection element as claimed in claim 6, wherein the sleeve is cylindrical and is arranged to receive a cylindrical ossicular prosthesis foot.

8. The prosthetic connection element as claimed in claim 6, wherein the sleeve has a split cylindrical wall having a longitudinal split defined by entirely straight opposed edges of the split cylindrical wall, and the sleeve is arranged to receive a cylindrical ossicular prosthesis foot.

9. The prosthetic connection element as claimed in claim 2, wherein the flat body has a substantially circular central part having two opposing sides, from each of the two opposing sides of the substantially circular central part there outwardly extends therefrom a respective substantially rectangular symmetrical part.

10. The prosthetic connection element as claimed in claim 1, wherein, if the prosthetic connection element is not already connected to the foot of the middle ear ossicular prosthesis, a means is provided enabling the prosthetic connection element to be connected to the foot of the middle ear ossicular prosthesis.

11. A prosthetic connection element as claimed in claim 1, wherein if the prosthetic connection element is not already connected to the foot of the middle ear ossicular prosthesis a sleeve is fixed to the flat body, the sleeve being adapted to receive the foot of the middle ear ossicular prosthesis to ensure a connection with said foot by squeezing the sleeve.

12. The prosthetic connection element as claimed in claim 11, wherein the sleeve is cylindrical and is arranged to receive a cylindrical ossicular prosthesis foot.

13. The prosthetic connection element as claimed in claim 1, wherein the at least two pointed projections are six in number.

14. The prosthetic connection element as claimed in claim 1, wherein the flat body has a substantially circular central part having two opposing sides, from each of the two opposing sides of the substantially circular central part there outwardly extends therefrom a respective substantially rectangular symmetrical part.

15. A prosthetic connection element for connecting a stapes footplate of a human patient to a middle ear ossicular prosthesis, the prosthetic connection element being of biocompatible material and forming part of a foot of said middle ear ossicular prosthesis or being connected or connectable to said foot, the prosthetic connection element comprising
    a flat body, the flat body having a substantially circular central part having two opposing sides, from each of the two opposing sides of the substantially circular central part there outwardly extends therefrom a respective substantially rectangular symmetrical part, the flat body sized to rest on the stapes footplate such that when the flat body rests on the stapes footplate the flat body does not extend beyond edges of the stapes footplate, the flat body provided with
        a flat surface having an area sufficient to prevent reabsorption of osseous tissue of the stapes footplate, and
        at least two pointed projections, the at least two pointed projections individually projecting downwardly, distally, and directly from edges of said flat body and away from said flat body, wherein each of said at least two pointed projections has a tapered pointed end distal to the flat body to penetrate the stapes footplate.

16. The prosthetic connection element as claimed in claim 15, wherein the flat body has an axis of symmetry, the at least two pointed projections being distributed symmetrically about said axis of symmetry.

17. A prosthetic connection element as claimed in claim 16, wherein the flat body has a second axis of symmetry perpendicular to the first axis of symmetry, the at least two pointed projections being distributed symmetrically about both the first and second axes of symmetry.

18. The prosthetic connection element as claimed in claim 16, wherein the flat surface extends continuously across the axis of symmetry.

19. The prosthetic connection element as claimed in claim 16, wherein, if the prosthetic connection element is not already connected to the foot of the middle ear ossicular prosthesis, a means is provided enabling the prosthetic connection element to be connected to the foot of the middle ear ossicular prosthesis.

20. The prosthetic connection element as claimed in claim 16, wherein if the prosthetic connection element is not already connected to the foot of the middle ear ossicular prosthesis a sleeve is fixed to the flat body, the sleeve being adapted to receive the foot of the middle ear ossicular prosthesis to ensure a connection with said foot by squeezing the sleeve.

21. The prosthetic connection element as claimed in claim 20, wherein the sleeve is cylindrical and is arranged to receive a cylindrical ossicular prosthesis foot.

22. The prosthetic connection element as claimed in claim 20, wherein the sleeve has a split cylindrical wall having a longitudinal split defined by entirely straight opposed edges of the split cylindrical wall, and the sleeve is arranged to receive a cylindrical ossicular prosthesis foot.

23. The prosthetic connection element as claimed in claim 15, wherein, if the prosthetic connection element is not already connected to the foot of the middle ear ossicular prosthesis, a means is provided enabling the prosthetic connection element to be connected to the foot of the middle ear ossicular prosthesis.

24. A prosthetic connection element as claimed in claim 15, wherein if the prosthetic connection element is not already connected to the foot of the middle ear ossicular prosthesis, a sleeve is fixed to the flat body, the sleeve being adapted to receive the foot of the middle ear ossicular prosthesis to ensure a connection with said foot by squeezing the sleeve.

25. The prosthetic connection element as claimed in claim 24, wherein the sleeve is cylindrical and is arranged to receive a cylindrical ossicular prosthesis foot.

26. The prosthetic connection element as claimed in claim 15, wherein the at least two pointed projections are six in number.

* * * * *